United States Patent [19]

Nelson et al.

[11] Patent Number: 4,788,150
[45] Date of Patent: Nov. 29, 1988

[54] LIQUID HANDLING

[75] Inventors: Larry A. Nelson; William A. Mace, both of Spokane, Wash.

[73] Assignee: Fisher Scientific Company, Pittsburgh, Pa.

[21] Appl. No.: 27,558

[22] Filed: Mar. 18, 1987

Related U.S. Application Data

[62] Division of Ser. No. 706,070, Feb. 27, 1985, Pat. No. 4,670,219.

[51] Int. Cl.[4] ................. G01N 35/04; G01N 37/00
[52] U.S. Cl. ................. 436/45; 324/61 R; 324/61 QL; 422/63; 422/72; 422/100; 436/47
[58] Field of Search ................. 422/63–67, 422/100, 102; 436/45, 47; 324/60, 60 C, 61 R, 61 QL; 356/73, 318, 334, 338, 339, 341

[56] References Cited

U.S. PATENT DOCUMENTS

| | | |
|---|---|---|
| Re. 29,880 | 1/1979 | Duff . |
| 3,617,222 | 11/1971 | Matte . |
| 3,811,842 | 5/1974 | Diebler . |
| 3,856,470 | 12/1974 | Cullis . |
| 4,054,416 | 10/1977 | Duff ................. 422/64 |
| 4,095,174 | 6/1978 | Ishido . |
| 4,135,883 | 1/1979 | McNeil . |
| 4,260,581 | 4/1981 | Sakurada ................. 422/65 |
| 4,298,571 | 11/1981 | DiFulvio . |
| 4,311,667 | 1/1982 | Gocho . |
| 4,313,735 | 2/1982 | Yamashita . |
| 4,341,736 | 7/1982 | Drbal . |
| 4,344,768 | 8/1982 | Parker . |
| 4,360,360 | 11/1982 | Chiknas . |
| 4,363,781 | 12/1982 | Akamatsu . |
| 4,483,823 | 11/1984 | Umetsu et al. ................. 422/64 |
| 4,517,160 | 5/1985 | Galle . |
| 4,558,946 | 12/1985 | Galle et al. ................. 422/102 |
| 4,737,812 | 2/1983 | Stein . |

OTHER PUBLICATIONS

Hitachi 705 (1981).

*Primary Examiner*—Michael S. Marcus

[57] ABSTRACT

An analysis system has a first region in which sample materials are stored at an appropriate storage temperature and an analysis region which is maintained at a controlled and stabilized temperature higher than the temperature of the first region. Transfer mechanism for transferring a quantity of sample material from the first region for loading into an analysis cuvette in the analysis region includes a liquid handling probe that is mounted on a probe transport carriage, and a drive for moving the transport carriage between the first and second regions. The transport carriage includes a storage chamber connected to the liquid handling probe, thermal energy supplying means in heat exchange relation with the storage chamber, and thermal sensor means carried by the transport carriage. Means responsive to the thermal sensor supplies thermal energy to the transport carriage to maintain the storage chamber at substantially the same temperature as the analysis region.

17 Claims, 5 Drawing Sheets

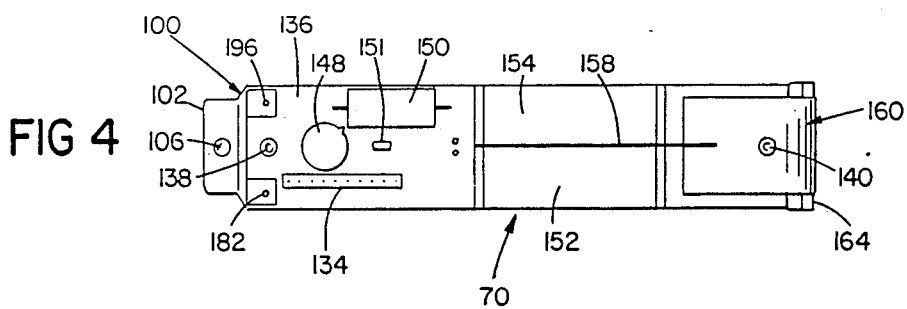
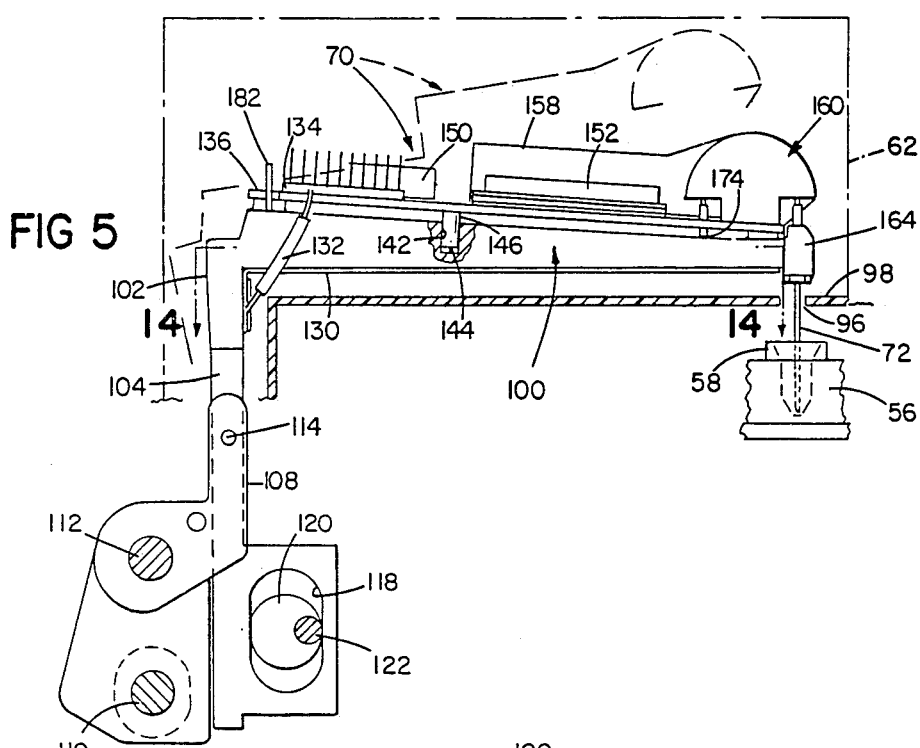
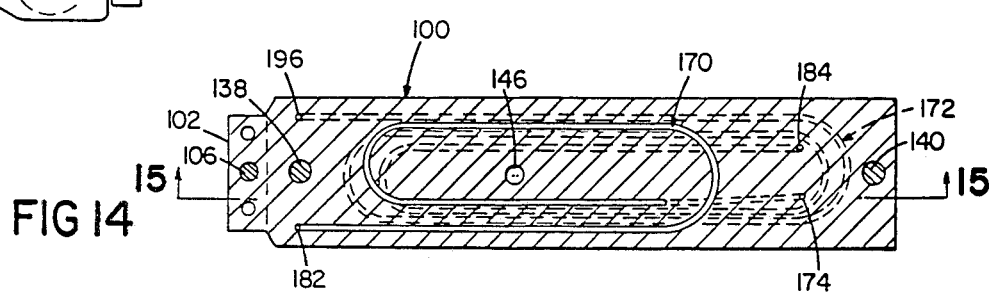
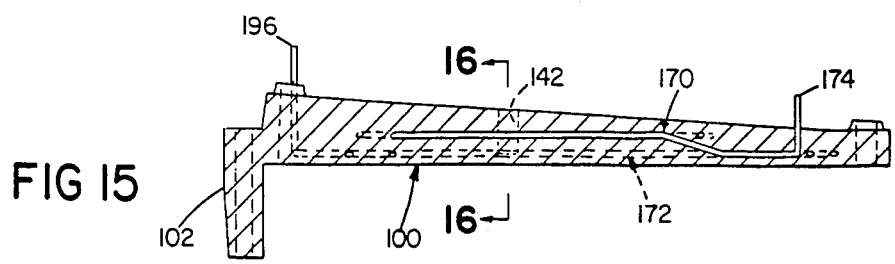

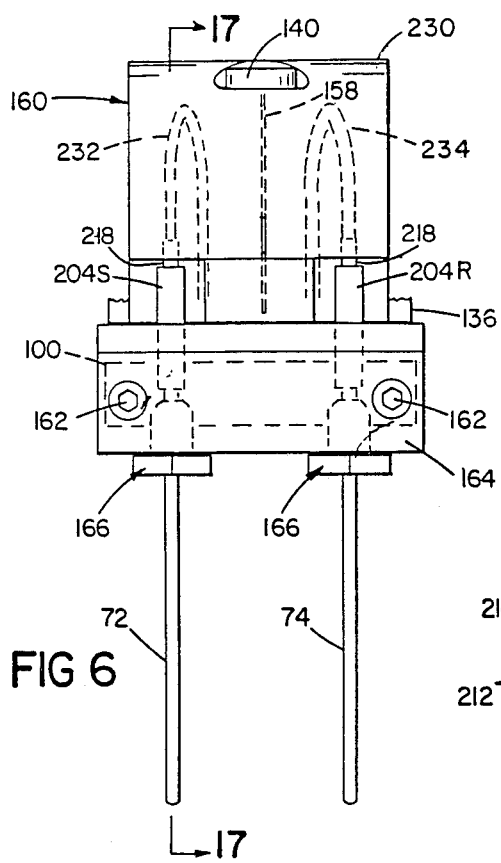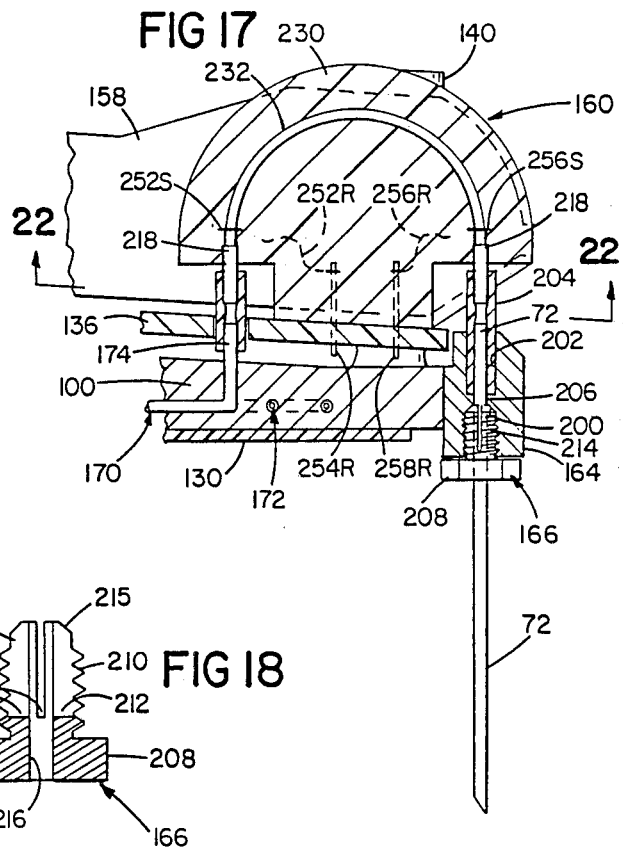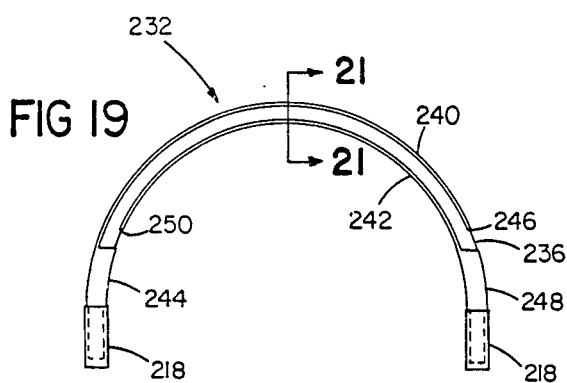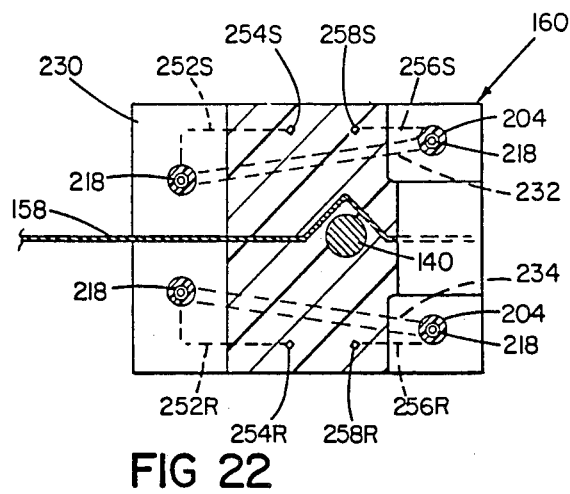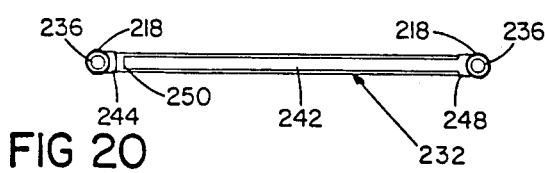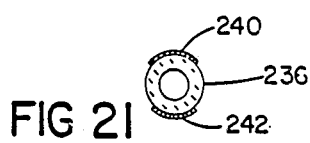

LIQUID HANDLING

This is a divisional of application Ser. No. 706,070, filed Feb. 27, 1985, now U.S. Pat. No. 4,670,219.

This invention relates to liquid handling systems, and to apparatus for the analysis of fluid samples, and has particular application to apparatus for the analysis of constituents of biological fluids such as blood.

Clinical analyzers are useful in performing a variety of analyses, including kinetic and endpoint analyses, by techniques such as absorption, light scattering, and/or fluorescence. Many chemical analyses must be conducted at controlled and stable temperatures as the involved chemical reactions are temperature sensitive. In conventional clinical analysis systems, for example, raw or dilute sample is mixed with one or more reactants for analysis, and the resulting mixture is maintained in an incubator region to bring the mixture to the desired analysis temperature, for example, 37° C., a temperature substantially higher than the temperature at which sample and reagent materials are usually stored. Clinical analyzers of the centrifugal type, in general, utilize a multicuvette rotor assembly which has a centrifugal array of spaced elongated radially extending cuvettes, each of which has an inner chamber for initially holding a first reactant which is frequently a sample of blood or other biological fluid, and an outer chamber for initally holding one or more different reactants. The two chambers are separated by divider structure, and the reactants are transferred by centrifugal force to an analysis region at the outer end of the cuvette for mixing and reaction and subsequent analysis. Small quantities of sample (2-20 microliters) typically are loaded into the inner chambers and reactants in quantities of up to about 200 microliters are loaded into the outer chambers. After loading, each rotor is conventionally incubated to equilibrate the rotor and the reactants in its several cuvettes to analysis temperature, and after such incubation the contents of the rotor are analyzed. In a typical analysis sequence, the rotor assembly is first spun at 100 rpm, then accelerated to about 4000 rpm for about one second for transferring the reactants from the inner chamber, then braked for mixing the sample and reactants, and then brought up to an analysis speed (typically 500-1000 rpm) for analysis.

Such analyzers are commonly used for the analysis of biological fluids such as blood, blood plasma or serum components, and perform absorbance mode analyses for glucose, cholesterol, creatinine, total protein, calcium, phosphorous, enzymes, and the like; and fluorescence or light scattering mode analyses for glucose, bile acids, phenytoin, pheophylline, gentamycin and the like.

In accordance with one aspect of the invention, there is provided an analysis system which has a first region in which sample materials are stored at an appropriate storage temperature and a second region which is maintained at a controlled and stabilized temperature higher than the temperature of the first region. An analysis cuvette is in the second region, and transfer mechanism is provided for transferring a quantity of sample material from the first region for loading into the analysis cuvette in the second region. The transfer mechanism includes a liquid handling probe that is mounted on a probe transport carriage, and a drive for moving the transport carriage between the first and second regions. The transport carriage includes a storage chamber connected to the liquid handling probe, thermal energy supplying means in heat exchange relation with the storage chamber, and thermal sensor means carried by the transport carriage. Means responsive to the thermal sensor supplies thermal energy to the transport carriage to maintain the storage chamber at substantially the same temperature as the second region. Preferably, liquid sensor means of suitable type such as optical, conductive or capacitive type is carried by the transport carriage for sensing the presence of liquid in the region between the tip of the probe and the storage chamber. Liquid metering means is connected to the transport carriage, and control means is provided for operating the drive and metering means to draw a predetermined quantity of sample material for analysis into the probe and the storage chamber and to deliver the predetermined quantity to the analysis cuvette in the second region in temperature equilibrated condition.

In preferred embodiments, the transport carriage includes a thermal mass in the form of a metal cantilever arm with the liquid handling probe fixedly mounted at one end thereof, the temperature sensor embedded in the metal arm and the thermal energy supplying means including heating means distributed along the length of the cantilever arm in intimate thermal transfer relationship therewith. The storage chamber is an elongated tubular conduit embedded in the metal arm in coil form.

In a particular embodiment, sample and reagent materials are stored in the first region, two probes are mounted on the carriage, the transport carriage includes two storage chambers, one connected to each probe, and the control means operates drive and metering means to draw predetermined quantities of sample and reagent materials through the probes and into the storage chambers and deliver the predetermined quantities of sample and reagent materials to an analysis cuvette in the second region in temperature equilibrated condition. A plurality of analysis cuvettes are in the second region, together with an analysis station and a transport mechanism for transporting analysis cuvettes sequentially to the loading station where the cuvettes are loaded with sample and reagent materials and then to the analysis station for photometric analysis of the mixture of sample and reagent materials.

In accordance with another aspect, the liquid handling probe is a metal tube that is secured in the transport carriage in a through channel that includes a threaded portion and a tapered shoulder at one end of the threaded portion. Clamping means includes a clamping member that has a threaded body and a passage axially extending through the threaded body that is defined in part by a circumferential array of axially extending finger portions in the threaded body, each finger portion having a tapered surface at one end thereof. When the clamping member is threadedly secured in the through passage with the metal tube extending through the axially extending passage in the clamping member body, the tapered end surfaces of the finger portions engage the tapered shoulder and cam the finger portions inwardly to clamp the metal tube in the support member. This arrangement facilitates individual adjustment of each probe to position the probe tips in precise aligned relation.

In accordance with another aspect of the invention, a liquid sensor system is provided that includes a tubular member of dielectric material with electrically conductive plate elements on opposite sides of the tubular member to form an electrical capacitor of capacitance value that varies as a function of the fluid in the tube. In a particular embodiment, the tubular member is connected in a series flow path between a probe tip and a storage chamber in a transport carriage. Means for monitoring the capacitance value to provide an indication of the nature of the fluid in the probe and storage chamber includes means for cyclically charging and discharging the capacitor and monitoring the charge (or discharge) rate of the capacitor to provide an indication of the type of fluid in the tubular member.

In preferred embodiments, the tubular member is of cylindrical configuration and the capacitor plate elements are elongated electrodes that are plated on opposite sides of the tubular member, each electrode having an angular extent of about 90°. A variable frequency oscillator is coupled to a capacitor charge control circuit for repetitively charging and discharging the capacitor, and means are provided for adjusting the frequency of the oscillator so that particular fluids may be identified as a function of the rate of charge (or discharge) of the capacitor which in turn is a function of the dielectric (and/or conductivity) characteristics of the fluid in the tube. The sensor tube may be straight or of other shape and may be used in a variety of liquid sensing applications. In a particular embodiment, two such sensing units are mounted on the cantilever arm of the transport carriage between probe inlets and storage chambers. In that embodiment, a multicuvette analysis assembly of long thermal time constant material is employed, and small (less than one cubic centimeter), precise, operator-selected quantities of sample and reagent liquids are concurrently transferred (via the storage chambers) from supply containers to the analysis cuvette in a time interval of about one second, that time interval being sufficient for those sample and reagent materials to be equilibrated to the analysis temperature so that substantially no further thermal equilibration interval is needed. In that embodiment, the clinical analyzer is of the centrifugal type and uses a multicuvette rotor which has a circumferential array of spaced elongated radially extending plural chamber cuvettes, each of which has an inner chamber for initially holding a first reactant (frequently a sample of blood or other biological fluid), and an outer chamber for initially holding one or more different reactants. After the rotor is loaded, the reactants are transferred by centrifugal force to an analysis region at the outer end of the cuvette for mixing and reaction and subsequent analysis by photometric or other appropriate analysis technique.

Preferred embodiments of the invention provide a system in which sample and reagent are drawn concurrently through the probes and sensor tubes respectively into serially connected storage chambers in a heat exchanger arm where the temperatures of the sample and reagent liquids are rapidly increased from the relatively low storage temperature to the substantially higher analytical temperature so that the aspirated sample and reagent liquids are rapidly equilibrated to the analytical temperature during the approximately one-second duration of the movement of the transport arm from the sample and reagent stations to the loading station where the pipetted volumes of sample and reagent are dispensed into a thermally equilibrated analytical cuvette. As both the cuvette and the reaction constituents are at the analytical temperature when the constitutents are dispensed into the cuvette, no incubation interval is required for equilibration, and analysis of the loaded cuvettes may commence as soon as filling of the operator specified cuvettes has been completed. Should either the sample or reagent sensor signal that sample liquid or reagent liquids have not been properly drawn into the storage chambers, the loading sequence is terminated or otherwise rescheduled, the aspirated materials are flushed, and the system automatically commences the next transfer sequence.

Other features and advantages of the invention will be seen as the following description of a particular embodiment progresses, in conjunction with the drawings, in which:

FIG. 4 is a top plan view of the transfer arm assembly of the analyzer;

FIG. 5 is a side elevational view of the transfer arm assembly and portions of its drive mechanism;

FIG. 6 is a front view of the transfer assembly;

FIG. 14 is a sectional view through the transfer arm taken along the line 14—14 of FIG. 5;

FIG. 15 is a sectional view of the transfer arm casting taken along the line 15—15 of FIG. 14;

FIG. 17 is a sectional view taken along the line 17—17 of FIG. 6;

FIG. 18 is a sectional view of the clamping bolt;

FIG. 19 is a side elevational view of the sample sensor tube;

FIG. 20 is a bottom view of the sensor tube shown in FIG. 17;

FIG. 21 is a sectional view taken along the line 21—21 of FIG. 20;

FIG. 22 is a bottom view of the sensor assembly taken along the line 22—22 of FIG. 17;

DESCRIPTION OF PARTICULAR EMBODIMENT

Figure 1:
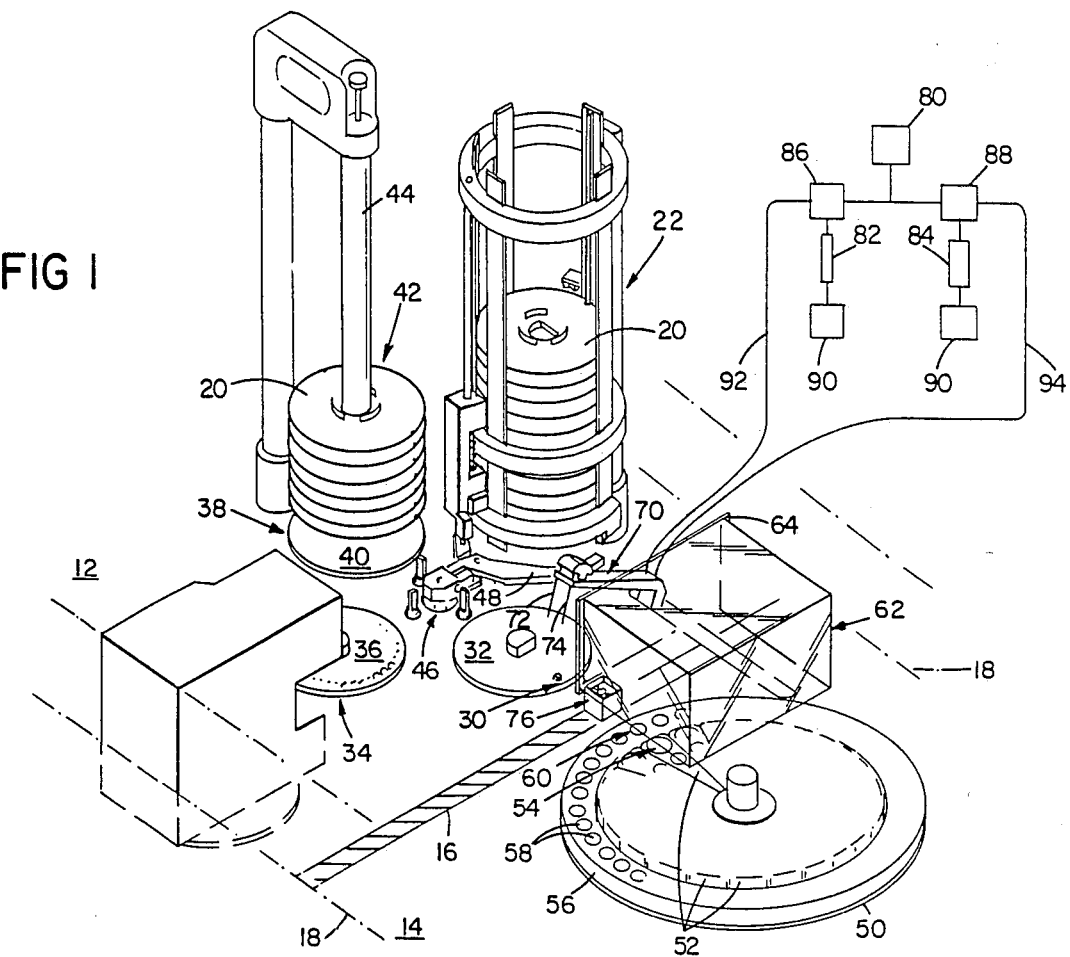
FIG. 1 is a diagrammatic and partly perspective view of portions of a centrifugal analyzer system in accordance with the invention.
Figure 2:
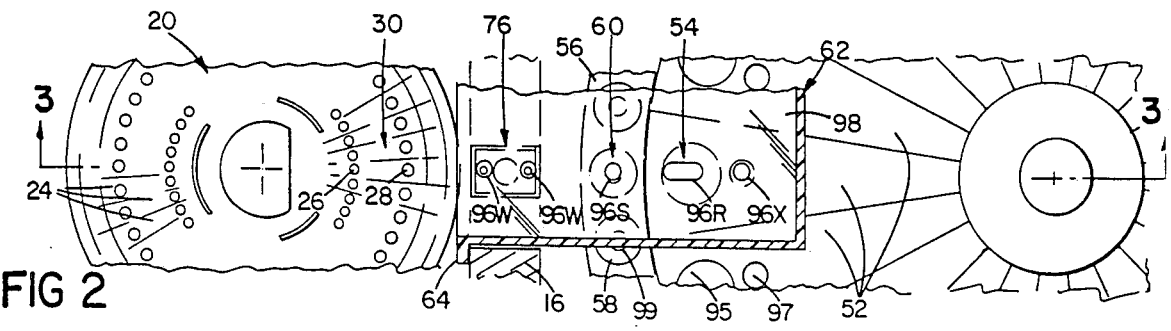
FIG. 2 is a top plan view of portions of the analytical and storage compartments of the analyzer shown in FIG. 1.
Figure 3:
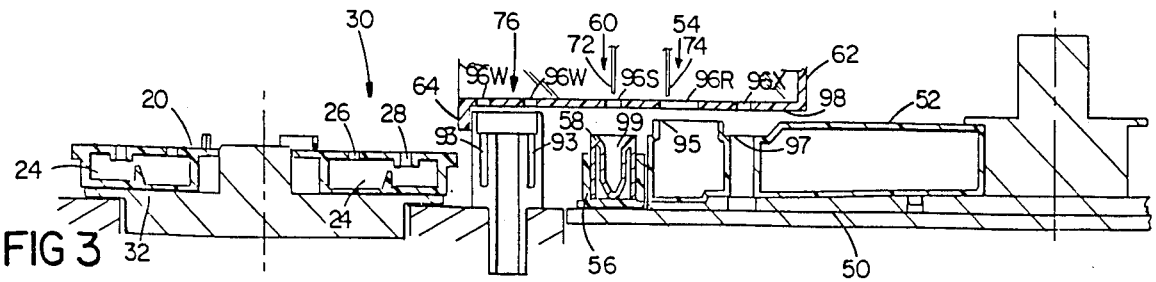
FIG. 3 is a sectional view taken along the line 3—3 of FIG. 2.

With reference to FIGS. 1–3, the analysis system thereshown is of the centrifugal type and has analytical compartment 12 and sample/reagent storage compartment 14 that are separated by thermal isolation wall 16 and surrounded by thermal insulation walls diagrammatically indicated at 18. Disposed in analytical compartment 12 are a stack of analysis rotors 20 of the type shown in co-pending application Ser. No. 615,644 filed May 31, 1984 entitled CENTRIFUGAL ANALYZER ROTORS, now U.S. Pat. No. 4,580,897 the disclosure of which is incorporated herein by reference. Rotors 20 in analystical compartment 12 are maintained at a precise user specified analytical temperature of 25°, 30° or 37° C. (plus or minus 0.3° C.) by a recirculating flow of temperature stabilized air through compartment 12 as described in greater detail in co-pending application Ser. No. 706,072 filed concurrently herewith and entitled ANALYSIS SYSTEM, now U.S. Pat. No. 4,708,886 the disclosure of which is incorporated herein by reference. Storage compartment 14 is maintained at a temperature that is substantially cooler than analysis compartment, for example 14°-15° C. (plus or minus 2° C.) by a similarly circulating stream of temperature stabilized air.

The supply of analysis rotors 20 are stored in analysis compartment 12 in spaced stacked relation in feeder tower 22. Each rotor 20 provides a circumferential array of thirty-nine analysis cuvettes 24, each of which has two loading ports 26, 28. The rotors 20 are of a long thermal time constant ultraviolet transmitting plastic so that the lower rotors in the stack in feeder tower 22 are at equilibration with the temperature of the analysis compartment 12. Also in compartment 12 is loading station 30 at which is disposed an indexable rotor support table 32 that is indexed by a stepper motor not shown; analysis station 34 that includes rotor support table 36 that is driven in rotation by a DC drive (not shown); park station 38 that includes a fixed rotor support table 40; discard stack 42 that includes receiving post 44 on which used rotors are received; and transport mechanism 46 for transporting rotors 20 from station to station, mechanism including caliper assembly 48 that has a pair of articulated arms that pick up and release rotors 20. Further details of this transport and rotor handling system may be had with reference to co-pending application Ser. No. 706,073 filed concurrently herewith entitled CUVETTE HANDLING, now U.S. Pat. No. 4,738,825 the disclosure of which is incorporated herein by reference.

Disposed in storage compartment 14 is reagent table 50 on which an array of twenty reagent containers 52 (each of twenty milliliters capacity) are disposed and moved past reagent station 54 by an indexing motor (not shown); and transport ring 56 which holds forty-four one-quarter milliliter sample cups 58 and is moved by indexing mechanism (not shown) past sample station 60. Isolation chamber 62 is movable between an operative position (as shown in FIG. 1) in which flange 64 is seated against isolation wall 16 and chamber 62 extends over the reagent and sample stations 54, 60, and a retracted position in which chamber 62 is retracted into analysis compartment 12 so that operator access may be obtained to reagent table 50 and sample ring 56 in storage compartment 14.

Mounted for movement within isolation chamber 62 is transfer arm mechanism 70 that carries pipette tubes 72, 74 at its forward end and has a drive of the type shown in co-pending application Ser. No. 599,509 filed Apr. 12, 1984 entitled LIQUID HANDLING, now U.S. Pat. No. 4,761,268 the disclosure of which is incorporated herein by reference, for moving transfer arm 70 between reagent station 54, sample station 60, wash station 76 disposed in isolation wall 16, and loading station 30 where the tips of pipette tubes 72, 74 are aligned with cuvette loading ports 26, 28.

Diluent (distilled water) is stored in reservoir 80 that is connected to metering pumps 82, 84 via three way valves 86, 88. Sample metering pump 82 has a capacity of one hundred microliters and reagent metering pump 84 has a capacity of two-hundred fifty microliters, and each metering pump includes a piston that is driven by a precision stepping motor 90. Metering pump 82 is connected to probe 72 through tubing 92 and cantilever arm 70 and metering pump 84 is connected to probe 74 through tubing 94 and arm 70.

Further details of the reagent, sample, wash and loading stations may be seen with reference to FIGS. 2 and 3. Isolation chamber 62 has a series of five aperture ports 96 in its bottom wall 98—apertures 96W being aligned with wash station 76; aperture 96S being aligned with sample station 60; aperture 96R being aligned with reagent station 54; and aperture 96X being aligned with the dry well 97 of the reagent container 52. Transfer arm 70 is moved within isolation chamber 62 and the probes 72, 74 are inserted through apertures 96 by the drive mechanism shown in FIG. 5. Wash station 76 has two cylindrical wells 93 for receiving the tips of pipette tubes 72, 74, each reagent container 52 has port 95 and dry well 97; and each sample cup 58 has a port 99.

Further details of pipette transfer assembly 70 may be seen with reference to FIGS. 4 and 5. The pipette transfer assembly includes aluminum casting arm 100 that has a length of about 12.5 centimeters, a width of about 2.3 centimeters and a graduated depth to a dimension of about ¼ centimeter at its forward end. Depending portion 102 at its rear end is secured to upstanding drive member 104 by bolt 106 and dowel pins. The drive mechanism is of the type shown in the above referenced copending patent application Ser. No. 599,509 and includes support frame 108, stepping motor driven lead screw 110 and guide shaft 112. Drive member 104 is pivotally mounted on support 108 by pivot shaft 114 which defines a pivot axis. Cam follower aperture 118 of drive member 104 cooperates with cam 120 that is mounted on shaft 122 that is driven in rotation by a stepping motor (not shown) to provide an angular lift of about 11° of transport carriage assembly 70 between the solid line and dotted line positions shown in FIG. 5.

Twenty-four ohm silicon insulated heater 130 is adhesively secured to the lower surface of aluminum arm 100 and connected via leads 132 to terminal block 134 that is mounted on support board 136 that is secured to arm 100 by fasteners 138, 140. Formed in casting 100 is socket 142 (FIG. 5) which receives thermistor 144 (YSI 44032 precision thermistor—30,000 ohms resistance at 25° C.) that is secured to board 136 by stand off 146. Also mounted on board 136 is voltage regulator 148, decoupling and power supply capacitors 150, 151, liquid sensor circuits 152, 154 that are separated by copper shield 158, and liquid sensor assembly 160. Secured to the forward end of casting 100 by fasteners 162 (FIG. 6) is support block 164 which receives collet bolts 166 that clamp pipette tubes 72, 74.

Figure 7:
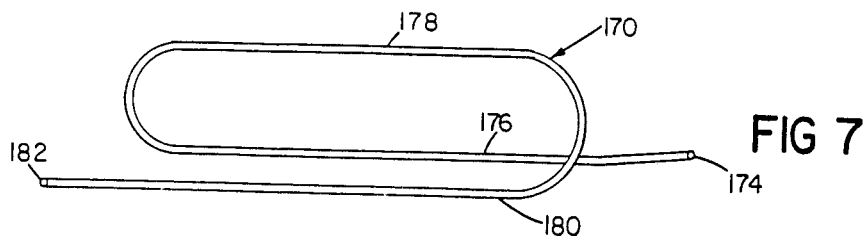
FIG. 7 is a top plan view of the sample storage chamber coil.
Figure 8:
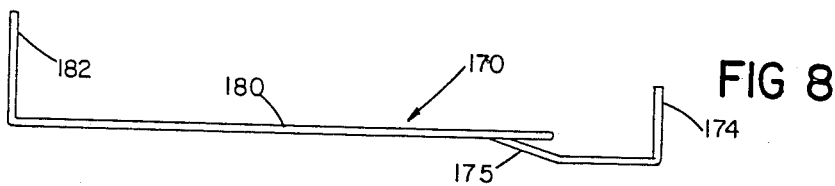
FIG. 8 is a side elevational view of the sample storage chamber coil shown in FIG. 7.
Figure 9:
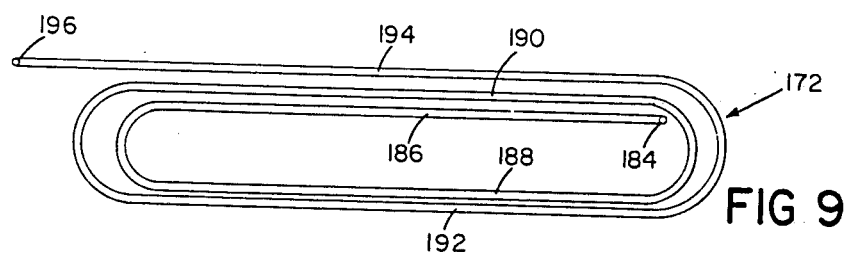
FIG. 9 is a top plan view of the reagent storage chamber coil.
Figure 10:
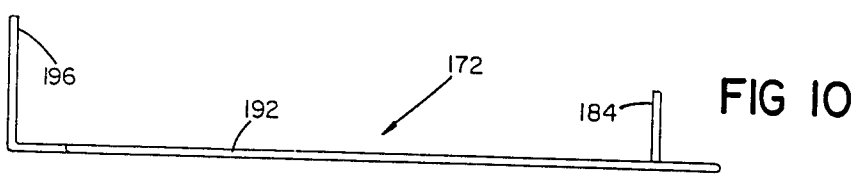
FIG. 10 is a side elevational view of the reagent storage coil shown in FIG. 9.
Figure 11:
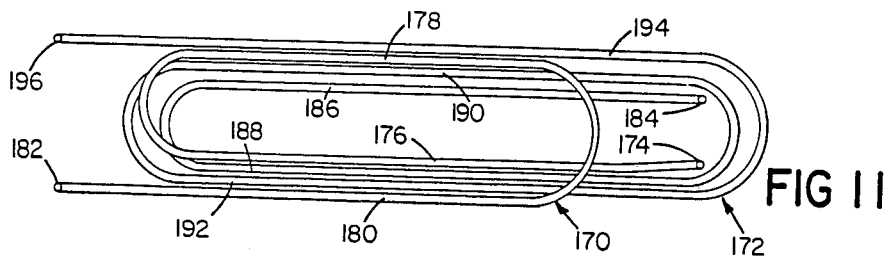
FIG. 11 is a top view of the sample and reagent storage coils in stacked spaced relation.
Figure 12:
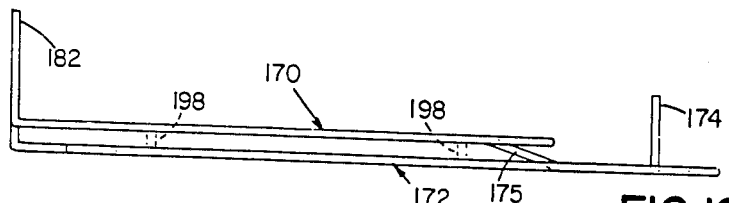
FIG. 12 is a side elevational view of the sample and reagent storage coils in stacked spaced relation.
Figure 13:
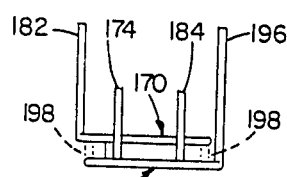
FIG. 13 is an end view of the stacked coils shown in top view FIG. 11.
Figure 16:
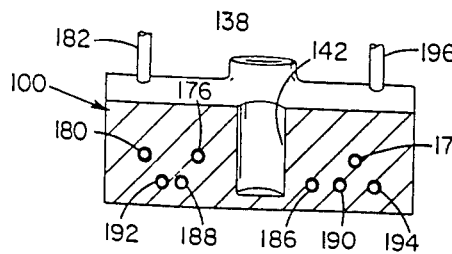
FIG. 16 is a sectional view taken along the line 16—16 of FIG. 15.

Cast within aluminum arm 100 are sample chamber coil 170 and reagent chamber coil 172, each of which is formed of nineteen gauge thin wall stainless steel tubing. As indicated in FIGS. 7 and 8, sample chamber coil 170 is of single turn configuration and extends from inlet 174 along inclined transition 175 and parallel sections 176, 178, 180 to outlet 182 and provides a chamber of about one-hundred microliters capacity. Reagent coil 172, as shown in FIGS. 9 and 10, is of double turn configuration and extends from inlet 184 through two turns that include parallel lengths 186, 188, 190, 192 and 194 to outlet 196 to provide a chamber of about two-hundred fifty microliters capacity. The sample and reagent coils 170, 172 are purged with nitrogen, crimped shut, secured in parallel spaced relation as indicated in FIGS. 11 and 12 by spacer members 198, disposed in a mold for casting in aluminum body 100, details of the resulting cast assembly being shown in FIGS. 14-16.

Further details of pipette support assembly may be seen with reference to FIGS. 6, 17 and 18. Each pipette tube 72, 74 is a 3.7 centimeters length of 21 gauge thin wall stainless steel tubing (about 0.8 mm outer diameter). Two bores extend through collet block 164, the lower section of each bore being threaded to receive collet bolt 166 and having a 45 degree cam surface 200; and upper portion of the bore being an enlarged cylinder 202 in which Tygon tube 204 is seated against smaller diameter intermediate shoulder 206. Collet bolt 166, as shown in FIG. 18, has hexagonal head portion 208, threaded body portion 210 with axially extending slots 212 that define spaced axially extending finger portions 214 each of which has a 45° end surface 215, and a through bore 216 in which the stainless steel pipette tube is disposed with its upper end extending into Tygon tube 204, as indicated in FIG. 17. Each pipette tube 72, 74 may be vertically adjusted over a range of about 0.3 centimeters as compensation for tolerance build up of the several parts of the pipette support assembly. Tightening of collet bolt 166 brings surfaces 200 and 215 into engagement and flexes fingers 214 inwardly to securely clamp the pipette tube. The upper end of connector tube 204 is received on a cooperating projecting metal sleeve 218 of the sensor assembly 160.

Further details of liquid sensor assembly 160 may be seen with reference to FIGS. 17 and 19-22. That sensing assembly includes molded urethane housing 230 which supports tubular sample liquid sensor 232 and tubular reagent liquid sensor 234. Each liquid sensor is of the configuration shown in FIGS. 19-21 and includes a tube 236 of suitable glass such as Corning 8870, Corning 8940 or Kimble R6 formed in a semi-circle of about one centimeter radius with a stainless steel sleeve 218 adhesively secured at each end of glass tube 36. The tube 236S for sample liquid sensor 232 has an outer diameter of about $\frac{1}{2}$ millimeter, an inner diameter of about $\frac{1}{4}$ millimeter, and defines a volume of about 1.5 microliters. The tube 236R for reagent liquid sensor 234 has an outer diameter of about $\frac{3}{4}$ millimeter, and a somewhat smaller wall thickness so that it defines a chamber volume of about six microliters. Formed along the semicircular length of each tube 236 on opposite sides thereof are silver electrode plates 240, 242 (DuPont 7713 silver ink), each of which has an angular extent of about 90° as indicated in FIG. 21. Capacitor plate 240 extends from plated cylindrical lead attachment area 244 along a tube length of about two centimeters with its other end 246 spaced about $\frac{3}{4}$ millimeter from plated lead attachment cylinder 248 for capacitor electrode 242, the other end 250 of electrode 242 being similarly spaced about $\frac{3}{4}$ millimeter from lead attachment cylinder 244. As indicated in FIGS. 17 and 22, lead 252 (No. 40 AWG) extends from attachment cylinder 244 to connector 254 which protrudes from urethane housing 230 (FIGS. 17 and 22); and a similar lead 256 extends from attachment cylinder 248 to connector pin 258. Connector pins 254S and 258S provide connections via support board 136 to sample sensor circuit 152 while leads 254R and 258R provide similar connections to reagent sensor circuit 154.

Figure 23:
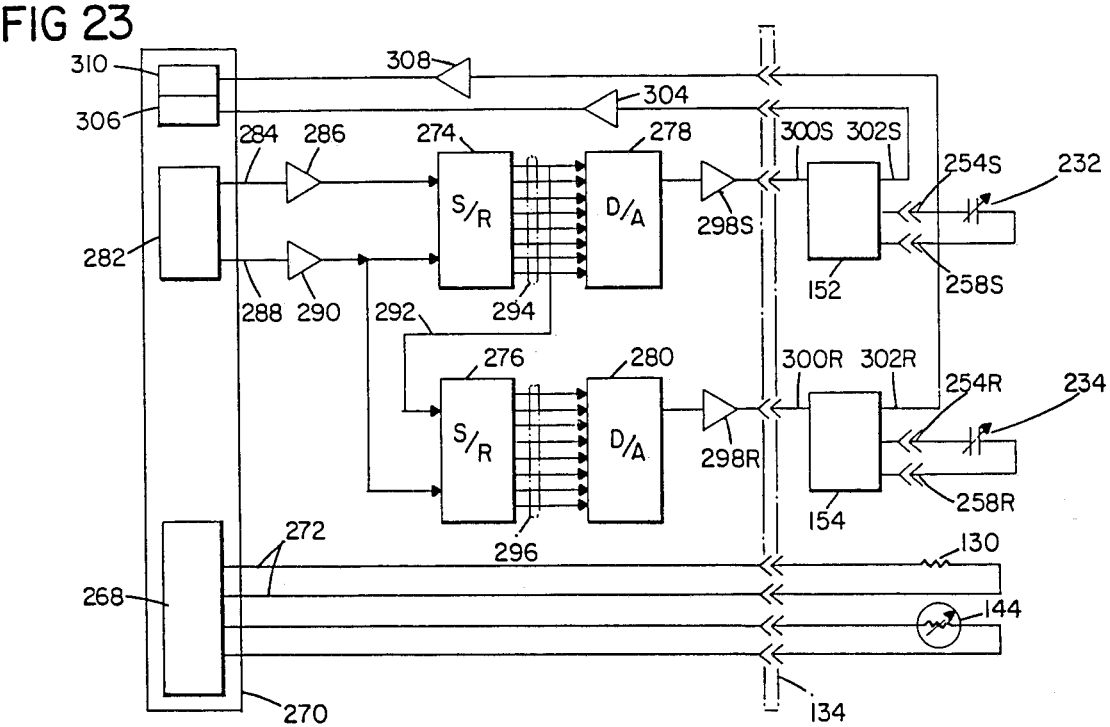
FIG. 23 is a block diagram of control circuitry associated with the transfer assembly.

Aspects of the control circuitry may be seen with reference to FIG. 23. In response to temperature signals from thermistor 144 applied via connector 134 to circuit 268 in system controller 270, circuit 268 produces an output over lines 272 through connector 134 to energize heater 130 and maintain aluminum pipette arm essentially at the temperature of analytical compartment 12. The control circuitry also includes cascaded shift registers 274, 276; and digital-to-analog converters 278, 280. Circuit 282 of controller 270 generates a serial data train signal over line 284 through buffer amplifier 286 to shift register 274; and in response to clock signals on line 288 supplied through buffer 290, that serial data train is shifted through register 274 and over line 292 to the cascaded shift register 276 to load shift registers 274, 276 with digital values. Those digital values specify a sample value that is applied over lines 294 to digital-to-analog digital converter 278 and a reagent value that is applied over lines 296 to digital-to-analog converter 280.

Converter 278 provides an analog output through amplifier 298 and connector 134 for application to input 300 of sample circuit 152 while the reagent control signal generated by digital-to-analog converter 280 is applied through amplifier 298R and connector 134 as input 300R of reagent circuit 154. Sample sensor capacitor 232 is connected to circuit 152 through connectors 254S, 258S and reagent sensor capacitor 232R is connected to circuit 154 through connectors 254R, 258R. Circuit 152 provides an output on line 302S through buffer 304 to sample indicator circuitry 306 in controller 270 while circuit 154 produces an output at terminal 302R through amplifier 308 to reagent indicator circuitry 310 in controller 270, and circuits 306, 310 may provide outputs to circuit 282 to adjust the sample and reagent signals being applied to circuits 152, 154.

Figure 24:
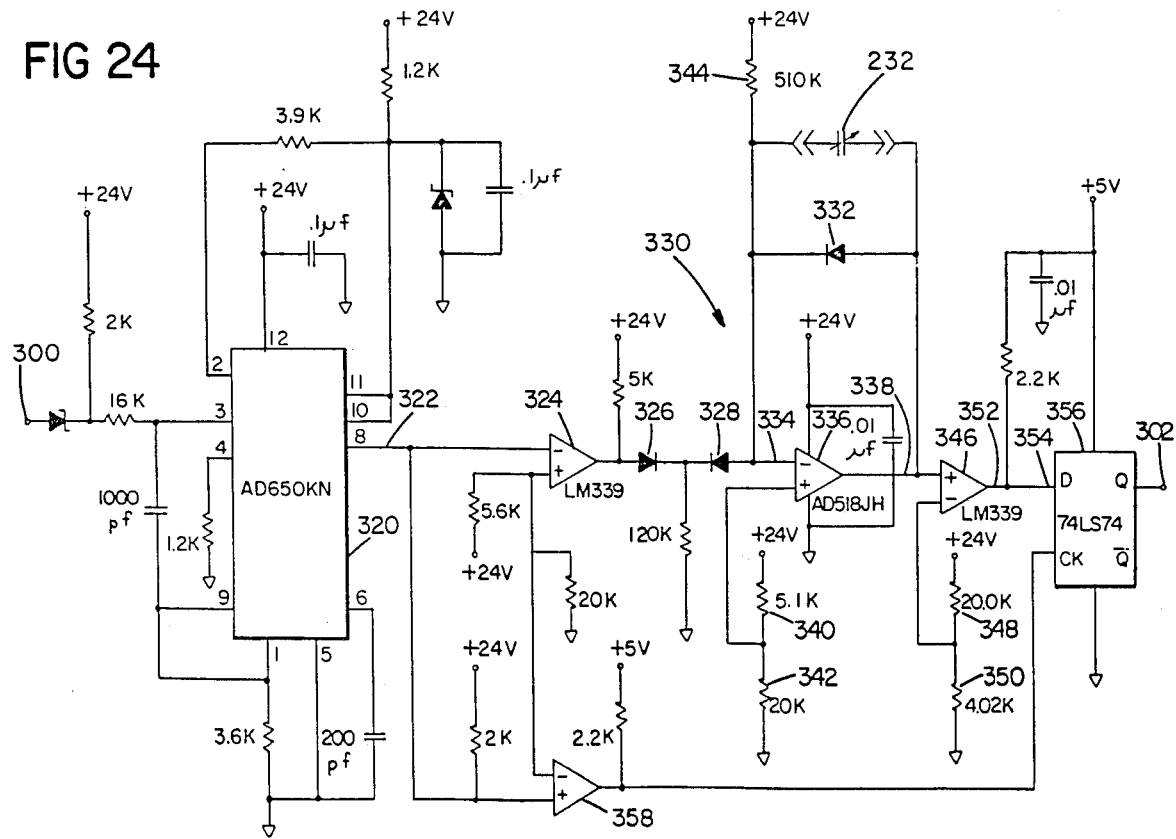
FIG. 24 is a schematic diagram of the liquid sensor circuitry.

Further details of the sample sensor circuitry may be seen with reference to the schematic diagram of FIG. 24 which shows the sample sensor hybrid integrated circuit 152 (the reagent sensor hybrid integrated circuit 154 being the same). The circuitry includes voltage controlled oscillator 320 that generates an unsymmetrical square wave output on line 322, the duration of the low portion of the square wave output on line 322 being variable as a function of the analog voltage applied to input terminal 300 by digital-to-analog converter 278. The square wave output on line 322 is applied through inverting comparator 324 and diode 326 to sensor circuitry 330 to which capacitor 232 is connected—in parallel with diode 332 between input 334 of operational amplifier 336 and output 338—the voltage at input 334 of operational amplifier 336 being controlled by the divider network of resistors 340, 342.

When the output of oscillator 320 on line 322 goes low, diode 326 is forward biased thereby reverse biasing diode 328. Capacitor 232 charges through resistor 344 at a rate proportional to its capacitance value and the output of operational amplifier 336 (on line 338) ramps downward at a rate inversely proportional to the value of capacitor 232 from a voltage of about 19.6 volts (determined by the voltage provided by divider network of resistors 340, 342).

The output voltage on line 338 is applied to comparator 346 which has a threshold established by the divider network of resistors 348 and 350, and when the voltage at output 338 falls below that value, comparator 344 produces an output on line 352 which conditions the data input 354 of latch 356.

When the output of oscillator 320 on line 322 goes high, a transition is applied through level shifting circuit 358 as a clock pulse to latch 356 to apply the flip flop data input at terminal 354 as an output on line 302 updating the liquid information to controller 270 over line 302. The high output from oscillator 320 is also applied through inverter 324 to reverse bias diode 326, allowing diode 328 to be forward biased and establishing a discharge current path for capacitor 232—capacitor discharging and the voltage at operational amplifier output 338 increasing until diode 332 becomes forward biased, thus limiting the output voltage at line 338 to about 19.8 volts and re-establishing the initial condition in the sensor capacitor 232 at the beginning of each charge cycle.

This circuitry thus provides continuous monitoring of the fluid in tube 236 of capacitor 232 and provides signals to controller 270 through buffer 304 (308). The system may establish fixed analog values that are provided by converters 278, 280 (and thus monitor the fluid in each capacitor tube for a particular type—a qualitative-type determination) or the system may vary the analog value to determine the type of fluid (a quantitative-type determination) drawn into the tube during each transfer cycle.

Sample capacitor 232 has a value of about two picofarads when its tube 220S is filled with air, a value of about 4.2 picofarads when its tube 220S is filled with diluent, and a value of about 5.5 picofarads when its tube 220S is filled with serum; and reagent capacitor 234 has a capacitance value of about 3.5 microfarads when its tube 220R is filled with air a value of about 7.7 picofarads when its tube 220S is filled with diluent, and a value of about 9.5 picofarads when its tube is filled with reagent. Thus the capacitance value of each sensor capacitor increases significantly when sample liquid or reagent liquid (as the case may be) is in its tube 220. These capacitance values are repetitively monitored (at rates in excess of ten thousand times per second) by measuring the rate at which the capacitors 232, 234 charge in response to negative transitions from voltage controlled oscillators 320. The frequencies of the square wave output from oscillators 320 are specified and changed by controller 270 through the shift registers 274, 276 and digital-to-analog converters 278, 280, to provide charge time duration values selected to provide triggering outputs from comparator 346 to latch 356 that indicate the type of fluid in the sensor tubes 220S and 220R.

In system operation, drive 110 positions arm 100 at the reagent and sample stations 54, 60 and drive 122 inserts the probe tips into containers 52, 58 at those stations. The liquid handling system pumps 82 and 84 draw sample and reagent concurrently through pipettes 72, 74, and the two capacitor sensor tubes 220S, 220R respectively into the serially connected storage chambers 172, 174 in the aluminum arm 100 where the temperatures of the sample and reagent liquids rapidly increase from the relatively low storage temperature of compartment 14 to the substantially higher operator selected temperature (25°, 30° or 37° C.) of analytical compartment 12 so that the aspirated sample and reagent liquids are rapidly equilibrated to the analytical temperature during the approximately one second duration of the movement of the transport arm 70 from the sample and reagent stations 60 and 54 to the loading station 30 where the pipetted volumes of sample and reagent are dispensed into the analytical cuvette 24 that is at the equilibrated temperature of the analytical compartment 12. The cuvette 24 and the reaction constituents thus are at the analytical temperature when the constitutents are dispensed into the cuvette (no incubation interval being required for equilibration) and the transport calipers 48 may move the loaded analysis rotor from loading station 30 to analysis station 34 as soon as filling of the operator specified cuvette regions has been completed. Should sample or reagent sensor circuit 154 or 156 signal controller 270 that sample liquid or reagent liquids have not been properly drawn into the storage chambers, controller 270 terminates or otherwise reschedules the loading sequence, the aspirated materials are dispensed into the wash station 76, pipettes 72, 74 are flushed and the next transfer sequence is automatically commenced.

While a particular embodiment of the invention has been shown and described, various modifications will be apparent to those skilled in the art, and therefore it is not intended that the invention be limited to the disclosed embodiment, or to details thereof, and departures may be made therefrom within the spirit and scope of the invention.

What is claimed is:

1. A method of operating an analysis system that has
   a first region in which sample materials are adapted to be stored.
   a second region in which an analysis cuvette is adapted to be disposed,
   transfer mechanism including a liquid handling probe, a probe transport carriage on which said liquid handling probe is mounted,
   a drive for moving said transport carriage between said first and second regions, said transport carriage including a solid body of thermally conductive material, sample material storage chamber structure embedded in said body and connected to said liquid handling probe, thermal energy supply means in heat exchange relation with said body, and thermal sensor means carried by said transport carriage, and
   liquid metering means connected to said storage chamber, said method comprising the steps of
   maintaining said first region at an appropriate storage temperature,
   disposing sample materials in said first region, disposing an analysis cuvette in said second region, maintaining said second region at an appropriate analysis temperature at least about 10° C. higher than said storage temperature such that said analysis cuvette is equilibrated to said analysis temperature,
   supplying thermal energy to said thermal energy supply means in response to said thermal sensor means to maintain said transport carriage body at said analysis temperature, and
   operating said drive and metering means to draw a predetermined quantity fo sample material for analysis from said first region through said probe into said storage chamber and to deliver said predetermined quantity of sample material to said analysis cuvette in said second region equilibrated in temperature to said analysis temperature in a time interval of about one second.

2. The method of claim 1 wherein said transport carriage body also includes reagent storage chamber structure to which a reagent handling probe and said metering means are connected and said method further includes the steps of disposing reagent material in said first region, and operating said metering means to concurrently draw predetermined quantities of sample and reagent materials from said first region into said sample and reagent storage chamber structure and to concurrently deliver said predetermined quantities of sample and reagent materials to said analysis cuvette in said second region equilibrated in temperature to said analysis temperature in a time interval of about one second.

3. A liquid sensor system comprising a tubular member of dielectric material for connection in a flow path of a liquid to be sensed, electrically conductive electrode elements fixedly-mounted on opposite sides of said tubular member to form an electrical capacitor of capacitance value that varies as a function of the fluid in said tube, and means for monitoring the capacitance value to provide an indication of the nature of the fluid in said probe and storage chamber, said capacitance monitoring means including means for repetitively monitoring the rate of change of charge on said capacitor to provide an indication of the type of fluid in said tubular member.

4. The system of claim 3 wherein said tube is of cylindrical configuration and said electrode elements are elongated electrodes that are plated along opposite sides of said tube, each said electrode having an angular extent of about 90°.

5. The system of claim 3 and further including a variable frequency oscillator for repetitively discharging said capacitor, and means for adjusting the frequency of said oscillator as a function of conductivity characteristics of the liquid to be monitored.

6. The system of claim 3 and further including structure defining a first region in which sample materials are adapted to be stored at an appropriate storage temperature, structure defining a second region in which an analysis cuvette is adapted to be disposed at an appropriate analysis temperature, transfer mechanism for transferring a quantity of sample material from said first region for loading into an analysis cuvette in said second region, said transfer mechanism including a liquid handling probe, a probe transport carriage on which said liquid handling probe and said tubular member are mounted, a drive for moving said transport carriage between said first and second regions, said transport carriage including a storage chamber connected to said liquid handling probe through said tubular member, thermal energy supplying means in heat exchange relation with said storage chamber, and thermal sensor means carried by said transport carriage, means responsive to said thermal sensor for supplying thermal energy to said thermal energy supplying means, liquid metering means connected to said transport carriage, and control means for operating said drive and metering means to draw a predetermined quantity of sample material for analysis into said probe and said storage chamber and to deliver said predetermined quantity to an analysis cuvette in said second region in temperature equilibrated condition.

7. The system of claim 6 wherein said transport carriage includes a body of thermally conductive material, said storage chamber structure being embedded in said body and said liquid handling probe and said tubular member being fixedly mounted at one end of said body.

8. The system of claim 7 wherein said temperature sensor embedded in said body and said thermal energy supplying means includes heating means distributed along the length of and in intimate thermal engagement with said body.

9. The analysis system of claim 8 wherein said storage chamber is an elongated tubular conduit that is disposed within said body and is connected between said metering means and said tubular member.

10. The system of claim 6 wherein said probe, said liquid sensor tubular member, and said storage chamber tube have similar inner diameters and the inner diameter of each is less than one millimeter.

11. The analysis system of claim 6 wherein said tubular member is of cylindrical configuration and said electrically conductive electrode elements are elongated electrodes that are plated along opposite sides of said tubular member, each said electrode having an angular extent of about 90°.

12. The system of claim 11 wherein said capacitance monitoring means includes means for repetitively charging said capacitor comprising a variable frequency oscillator, and means for adjusting the frequency of said oscillator to identify the liquid to be transferred from said first region to said second region as a function of its conductivity characteristics.

13. The system of claim 6 and further including two liquid sensor means carried by said transport carriage, each said liquid sensor means including a said tubular member connected to a corresponding probe for sensing the presence of liquid in the region between the tip of said probe and its storage chamber.

14. The system of claim 13 wherein said probes, said liquid sensor tubular members, and said storage chamber tubes have inner diameters of similar values and the inner diameter of each is less than one millimeter.

15. The system of claim 13 wherein each said liquid handling probe is an elongated metal tube, and further including a probe support portion on said body at one end thereof, said support portion having two through channels for receiving said metal tubes and cooperating tube clamping means that permits the axial position of each said elongated metal tube in said support portion to be axially adjusted.

16. The system of claim 15 wherein each said tubular member is of cylindrical configuration and said electrically conductive electrode elements are elongated electrodes that are plated along opposite sides of each said tubular member, each said electrode having an angular extent of about 90°.

17. The system of claim 16 wherein said capacitance monitoring means includes means for repetitively charging said capacitor comprising a variable frequency oscillator, and means for varying the frequency of said oscillator to identify the liquid to be transferred from said first compartment to said second compartment as a function of its dielectric characteristics.

* * * * *